United States Patent [19]

Kawashima et al.

[11] Patent Number: 5,583,215
[45] Date of Patent: Dec. 10, 1996

[54] CRYSTALLINE MIXTURE SOLID CONTAINING MALTITOL AND A PROCESS FOR PREPARING IT

[75] Inventors: Shigeru Kawashima; Mitsuo Magara; Yoshibumi Ishii, all of Shizuoka; Kazuaki Kato, Saitama, all of Japan

[73] Assignee: Towa Chemical Industry Co., Ltd., Tokyo, Japan

[21] Appl. No.: 280,813

[22] Filed: Jul. 26, 1994

Related U.S. Application Data

[63] Continuation-in-part of Ser. No. 836,017, filed as PCT/JP91/00696, May 23, 1991, Pat. No. 5,354,856.

[30] Foreign Application Priority Data

Jun. 25, 1990 [JP] Japan .................................. 2-164148
Feb. 26, 1991 [JP] Japan .................................. 3-53211

[51] Int. Cl.$^6$ .................................. C07H 15/04; C07H 3/04
[52] U.S. Cl. .................................. 536/127; 127/15; 127/16; 127/30; 127/58; 127/60; 568/863; 568/872; 426/658; 426/660
[58] Field of Search .................................. 536/127; 127/15, 127/16, 30, 58, 60; 568/863, 872; 426/658, 660

[56] References Cited

U.S. PATENT DOCUMENTS

| | | | |
|---|---|---|---|
| 4,408,041 | 10/1983 | Hirao et al. | 536/4.1 |
| 4,789,559 | 12/1988 | Hirao et al. | 426/658 |
| 4,831,129 | 5/1989 | Serpelloni | 536/124 |
| 4,846,139 | 7/1989 | Devos et al. | 127/46.2 |
| 4,849,023 | 7/1989 | Devos et al. | 127/40 |
| 4,917,916 | 4/1990 | Hirao et al. | 426/658 |
| 5,003,061 | 3/1991 | Carobbi et al. | 127/58 |
| 5,045,340 | 9/1991 | Kohler | 426/658 |
| 5,133,807 | 7/1992 | Decremoux | 127/58 |
| 5,141,859 | 8/1992 | Niimi et al. | 435/94 |

FOREIGN PATENT DOCUMENTS

| | | |
|---|---|---|
| 2581999 | 11/1986 | France . |
| 57-134498 | 8/1982 | Japan . |
| 61-180797 | 8/1986 | Japan . |
| 61-268696 | 11/1986 | Japan . |

OTHER PUBLICATIONS

English language translation of FR 2,581,999 (already of record).

*Primary Examiner*—Ronald W. Griffin
*Attorney, Agent, or Firm*—Beveridge, DeGrandi, Weilacher & Young

[57] ABSTRACT

The crystalline mixture solid containing maltitol of the present invention has a crushed and relatively tight crystal structure which can be observed at 1,000 magnifications by a scanning electron microscope, an apparent specific gravity in the range of 0.650–0.750, an oil absorptivity of the powdered crystalline mixture solid containing maltitol having a particle size from 50 mesh to 20 mesh in the range of 7.0%–17%, in other words, is relatively heavy in apparent specific gravity and low in oil absorptivity, and the crystalline mixture solid containing maltitol is prepared by continuously supplying an aqueous solution of maltitol to an extruder provided with elongated cooling and kneading zones, cooling and kneading it in the presence of seed crystals to form a maltitol magma, and continuously extruded from a nozzle.

5 Claims, 2 Drawing Sheets

FIG. IA
FIG. IB
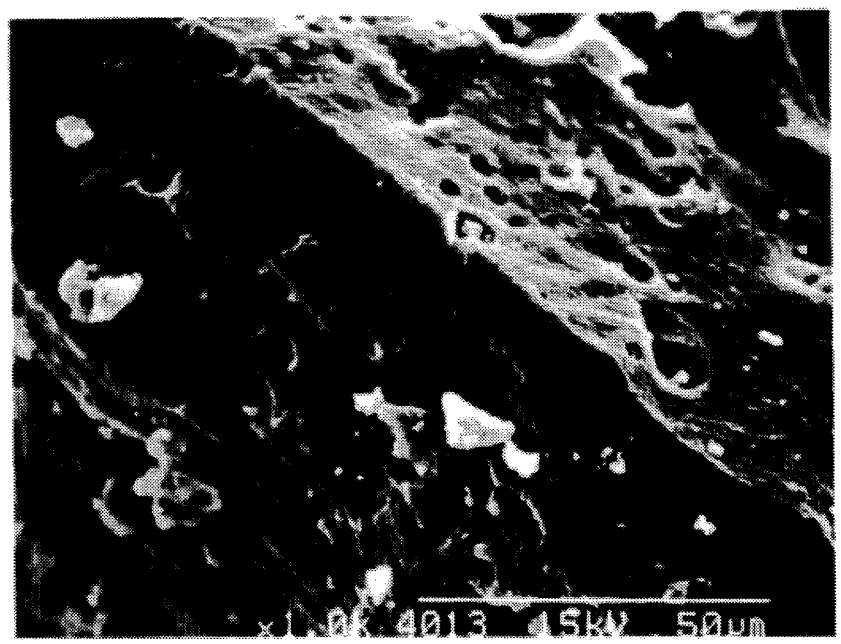

CRYSTALLINE MIXTURE SOLID CONTAINING MALTITOL AND A PROCESS FOR PREPARING IT

REFERENCE TO A RELATED APPLICATION

This is a continuation-in-part of our application Ser. No. 07/836,017, filed as PCT/JP91/00690, May 23, 1991, now U.S. Pat. No. 5,354,856, which is relied on and incorporated herein by reference in its entirety.

TECHNICAL FIELD

The present invention relates to a crystalline mixture solid containing maltitol and a process for producing it. Particularly, the present invention relates to a crystalline mixture solid containing maltitol having an improved physical properties and a process for producing it.

BACKGROUND ARTS

Sugar alcohols such as sorbitol and mannitol have hitherto been known to have crystals or crystalline mixture solids, and a variety of methods for producing them have already been known.

In contrast with mannitol or sorbitol of which cystals have hitherto been known, maltitol tends to form a supersaturated state more readily and thus hardly forms a crystal. The methods for producing a crystal or a crystalline mixture solid of it have been invented only recently, and it was believed impossible to produce a crystal from maltitol prior to this invention as described by JIRO NIKUNI, DENPUN KAGAKU HANDBOOK, lines 14 and 17–18 of p. 461 (published from ASAKURA SHOTEN, Jul. 20, 1977).

The crystals of maltitol or the crystalline mixture solid containing maltitol have been prepared for the first time in 1981, and the methods for producing them are disclosed in TOKKYO-KOKOKU-KOHO (Publication for Opposition of Examined Patent Application) SHOWA 63(1988)-2439.

The crystalline mixture solid containing maltitol holds a place in its commercial market more important than crystals obtained by the fractional crystallization method because of its excellent properties and for economical reasons.

The crystalline mixture solid containing maltitol, however, has many ambiguous points on the physical behaviors for producing its crystalline mixture solid, as it is not long since the discovery of the crystalline mixture solid containing maltitol and it tends to form a supersaturated state very easily. Therefore, the crystalline mixture solid containing maltitol was produced only by a limited method.

The method for producing the crystalline mixture solid containing maltitol disclosed in the aforementioned TOKKYO-KOKOKU-KOHO comprises dissolving maltitol having a purity of 65% or more (unless otherwise described, % means % by weight hereinafter) into water to form an aqueous solution of maltitol having a concentration of about 65–95%, and forming a mascuite by the co-existence of a seed crystal. Such method in itself is provided for any one of the well-known methods of a block grinding method, a fluidized drying method or a spray-drying method.

For example, the spray-drying method is generally a method which comprises spraying a mascuite having a concentration of about 70–85% and a crystallization rate in the range of about 25–60% from a nozzle of a high-pressure pump and maturing the sprayed mascuite under the hot air at a temperature of 60°–100° C. which will not cause the melting of crystalline powder for about 1–20 hours.

The block grinding method is generally a method which comprises standing a mascuite having a water content of about 5–15% and a crystallization rate in the range of 10–60% for 0.5–5 days to crystallize and solidify the whole of the mascuite in the form of a block, which is then ground by a grinding or cutting method and dried.

Among these methods, the block grinding method, in spite of its complicated processes, is used as a major method for producing the crystalline mixture solid containing maltitol for the reasons that each process can be carried out relatively readily and that the scale of the installation and the process costs are cheaper as compared with those of the other two methods.

The crystalline mixture solid containing maltitol obtained by these methods had an apparent specific gravity in the range of about 0.43–0.59 in the form of a powder having a particle size of 20–50 mesh and was lighter than the other sugar alcohols such as sorbitol or the like. Furthermore, the crystalline mixture solid containing maltitol had a high oil absorptivity in the range of 15–22%, and a relatively thin porous crystalline structure was observed with a scanning electron micrograph having a magnification of about 1,000.

The crystalline mixture solid containing maltitol prepared by the aforementioned conventional methods had many problems with its physical properties.

For example, (a) the crystalline mixture solid containing maltitol prepared by the conventional method was bulky in its volume because of its small apparent specific gravity, and a packaging material or a packaging vessel used for the other sugar alcohols and originally having a capacity satisfactory to hold a certain amount of such other sugar alcohols was insufficient to hold the full volume of the same weight of a crystalline mixture solid containing maltitol, so that a packaging material or a packaging vessel for its exclusive use is required and a large space or a conveying apparatus is also required for the storage or conveyance of it;

(b) the powder of it is light in weight and thus the fine powder tends to be scattered, so that its use is limited; and (c) it has a thin crystal structure, so that a tablet prepared by the direct punching of it tends to have an insufficient hardness.

There also remained many problems in the conventionally described fluidized drying method and the spray-drying method as well as the block grinding method which has been conventionally used.

For example, the fluidized drying method is a method in which the crystal of maltitol or the crystalline mixture solid containing maltitol are used as a fluidized bed, on which an aqueous solution of maltitol is blown to make granulation and drying. The method, however, has the problems that it has a low crystallization rate of maltitol and requires a relatively long time for the fluidized drying process, so that the apparatus is required to be enlarged and it is difficult to produce the crystalline mixture solid containing maltitol on a large scale.

When the spray-drying method was intended to be employed, it had the problems that it was difficult to adjust the crystallization rate on the preparation of the mascuite of maltitol, that the mascuite of maltitol which was sprayed into dry air caused insufficient growth of the crystal and the ratio of a glassy solid component was increased, that the powder thus produced adhered to the wall of a dryer by the influence of the insufficient growth of the crystal and could not be produced continuously, and that this method needed an expensive amount of installation cost.

On the other hand, the block grinding method is a currently employed method, which however has problems that (a) the processes are complicated and each process requires a long time, (b) containers and places for the storage of large amounts of intermediates in the middle of the crystallization are required, (c) hygienic considerations, installations and structures are required for their storage in the middle of the processes, and (d) each process of ten requires complicated operations and thus the automating or labor-saving of the process is difficult.

Therefore, a crystalline mixture solid containing maltitol in which these various problems have been solved and the conventional physical properties have been improved as well as a method for producing it are desired to be developed.

DISCLOSURE OF THE INVENTION

The present inventors have conducted earnest researches on the physical properties of the crystalline mixture solid containing maltitol and a process for producing it. As a result, they have produced a plastic maltitol magma from an aqueous solution of maltitol with an extruder having an elongated cooling and kneading zone and thus succeeded in the preparation of a crystalline mixture solid containing maltitol having improved physical properties in an extremely short time in a small apparatus by a method where labor and time are saved. They have thus accomplished the present invention.

That is, the present invention is, first, a crystalline mixture solid containing maltitol, comprising (a) having a crushed and relatively tight crystal structure which can be observed by a scanning electron microscope with magnifying power of ×1000, (b) having an apparent specific gravity of said crystalline mixture solid containing maltitol having a particle size from 50 mesh to 20 mesh in the range of 0.650–0.750, and (c) having an oil absorptivity of said crystalline mixture solid containing maltitol having a particle size from 50 mesh to 20 mesh in the range of 7.0%–17% and (d) having a melting point of said crystalline mixture solid containing maltitol in the range of 134°–145° C.

Second, the present invention is a crystalline mixture solid containing maltitol stated above, wherein the solid component comprises maltitol in the range of 80–98% by weight, sorbitol in the range of 0.5–15% by weight, and maltotriitol and sugar alcohols having a degree of polymerization not less than that of maltotriitol, i.e. DP≧3, in the range of 1.5–10% by weight.

Third, the present invention is a crystalline mixture solid containing maltitol having a melting point in the range of 134°–145° C. which is prepared by supplying an aqueous solution of maltitol to an extruder provided with elongated cooling and kneading zones, cooling and kneading the aqueous solution of maltitol in the presence of seed crystals to form a maltitol magma, and extruding continuously said magma from a nozzle.

Fourth, the present invention is a crystalline mixture solid containing maltitol having a melting point in the range of 134°–145° C. which is prepared by continuously supplying an aqueous solution of maltitol having a concentration in the range of 80–98% by weight and a maltitol content in the solid component in the range of 80–99% by weight to the first zone of an extruder provided with elongated cooling and kneading zones, cooling and kneading the aqueous solution of maltitol to 50°–90° C., continuously or intermittently conducting the addition and kneading of seed crystals in an amount of 3–80% by weight based on the extruded amount to the second zone in which said aqueous solution of maltitol has been cooled to a temperature of 50°–80° C., further continuing cooling and kneading in the continuous third zone, cooling and kneading to a temperature of 25°–60° C. in the final zone, and continuously extruding a maltitol magma thus formed from an extrusion nozzle.

Fifthly, the present invention is a crystalline mixture solid containing maltitol which is prepared by sequentially passing through the following steps of (a) the first step in which an aqueous solution of maltitol having a concentration of 80–98% by weight and a solid composition comprising 0.5–15% by weight of sorbitol, 80–98% by weight of maltitol and 1.5–10% by weight of maltotriitol and sugar alcohols having a molecular weight not less than that of maltotriitol (DP≧3) is continuously supplied to the first zone provided with elongated cooling and kneading zone, cooling and kneading to a temperature of 50°–90° C. is conducted, the addition and kneading of seed crystals in an amount of 3–80% by weight based on the extruded amount to the second zone in which the temperature reached 50°–80° C. are continuously or intermittently conducted, cooling and kneading are further continued in the continuous third zone, the mixture is cooled and kneaded to a temperature of 25°–60° C. in the final zone, and a maltitol magma formed is extruded from an extrusion nozzle, (b) the second step in which said maltitol magma extruded is matured at 15°–80° C. for 5–30 minutes, and (c) the third step in which the matured maltitol magma is then roughly ground, dried under the conditions at 80°–115° C. for 60 minutes or more, pulverized and classified.

Sixthly, the present invention is a process for preparing crystalline mixture solid containing maltitol, comprising supplying continuously an aqueous solution of maltitol to an extruder provided with elongated cooling and kneading zones, growing a maltitol magma by cooling and kneading said aqueous solution of maltitol in the presence of seed crystals and continuously extruding said maltitol magma from a nozzle.

Seventhly, the present invention is a process for preparing a crystalline mixture solid containing maltitol, comprising supplying an aqueous solution of maltitol having a concentration in the range of 80–98% by weight and a maltitol content in the solid component in the range of 80–99% by weight to the first zone of an extruder provided with elongated cooling and kneading zones, cooling and kneading it to 50°–90° C., continuously or intermittently conducting the addition and kneading of seed crystals in an amount of 3–80% by weight based on the extruded amount to the second zone in which said aqueous solution of maltitol has been cooled to a temperature of 50°–80° C., further continuing cooling and kneading in the continuous third zone, cooling and kneading to a temperature of 25°–60° C. in the final zone, and continuously extruding a maltitol magma thus formed from an extrusion nozzle.

Eighthly, the present invention is a process for preparing a crystalline mixture solid containing maltitol which is prepared by sequentially passing through the following steps of (a) the first step in which an aqueous solution of maltitol having a concentration of 80–98% by weight and a solid composition comprising 80–98% by weight of maltitol is continuously supplied to the first zone provided with elongated cooling and kneading zone, cooling and kneading to a temperature of 50°–90° C. are conducted, seed crystals in an amount of 3–80% by weight based on the extruded amount are continuously or intermittently added and kneaded to the second zone in which the temperature reached 50°–80° C., cooling and kneading are further continued in the continuous third zone, the mixture is cooled and kneaded to a temperature of 25°–60° C. in the final zone, and a maltitol magma formed is extruded from an extrusion nozzle, (b) the second step in which said maltitol magma extruded is matured at 15°–80° C. for 5–30 minutes, and (c) the third step in which the matured maltitol magma is then roughly ground, dried under the conditions at 80°–115° C. for 60 minutes or more, pulverized and classified.

Ninthly, the present invention is a process for preparing a crystalline mixture solid containing maltitol according to any one of the sixth through eighth embodiments above, wherein the aqueous solution of maltitol has a composition comprising 0.5–15% by weight of sorbitol, 80–98% by weight of maltitol and 1.5–10% by weight of maltotriitol and sugar alcohols having a molecular weight not less than that of maltotriitol (DP$\geq$3).

The present invention is described in detail below.

An extruder which can be employed in the present invention comprises an elongated cooling and kneading zone. While the extruder requires a structure where raw materials are continuously introduced, a seed crystal is introduced continuously or intermittently to form a plastic maltitol magma and the magma produced from a final cooling zone can be continuously discharged, the extruder must only have such a structure as to satisfy these conditions irrelative to its shape or the kneading, cooling, conveying or discharging modes.

For instance, a structure having kneading, cooling and conveying functions includes a structure of a single screw extruder, a structure of a twin-screw extruder, a structure of a rotary gear pump, a structure for conducting insertion into a cylindrical structure equipped with a fixed blade with a conveying device such as a piston of the like, all of which can be employed in the present invention.

Among these apparatuses, a commercially available extruder can be advantageously used for the achievement of the object of the present invention, and the typical apparatuses include an ALFALIZER (mfd. by SUEHIRO TEKKOSHO K. K.), a KRC KNEADER (mfd. by KURIMOTO TEKKOSHO K. K.), a TWIN-SCREW EXTRUDER (mfd. by KOWA KOGYO K. K.), extruders for various foods manufactured and marketed by NIHON SEIKOSHO K. K., and the like.

An aqueous solution of maltitol which can be employed in the present invention may be a solution having such a quality that a plastic maltitol magma is formed by cooling it in the presence of a seed crystal irrelative to the sources of its raw materials or the method for producing it. The aqueous solution is preferably a solution having a content of maltitol in the range of 80–99% in the solid content and a solid concentration in the range of 80–98%, as such a solution can easily form a maltitol magma.

Particularly, an aqueous solution of maltitol having a sugar composition of 0.5–15% of sorbitol, 80–98% of maltitol and 1.5–10% of maltotriitol and sugar alcohols having a molecular weight not less than that of maltotriitol (DP$\geq$3) and having a concentration of 80–98% is more preferred for the achievement of the object of the present invention as it can easily form a maltitol magma continuously. Among such solutions having the same sugar composition, an aqueous solution having a concentration in the range of 85–97% is further preferred.

When the amount of a sugar alcohol having DP$\geq$3 in the components of the aqueous solutions of maltitol exceeds 10%, a maltitol magma having a sufficient hardness is hardly formed, so that it is preferable to avoid the increase of the sugar alcohol components such as maltotriitol and sugar alcohols having a molecular weight not less than that of matotriitol.

Furthermore, the aqueous solution of maltitol used in this invention is not necessarily in the state of a clear solution and may be a solution in which crystals have been deposited and suspended prior to the supply of the solution to an extruder.

While the aqueous solution of maltitol is continuously supplied to the extruder in order to carry out the present invention, the aqueous solution of maltitol preferably has a temperature in the range of 50°–150° C. for the reasons that the solution can prevent the phenomena such as the decomposition of the aqueous solution of maltitol or the coloring due to the scorching, that the viscosity is decreased and the fluidity is increased to make the aqueous solution of maltitol easy to deal with, and that in such a range of temperature the maltitol magma is easily formed after the introduction of the solution into the extruder.

The supply rate of the aqueous solution of maltitol is largely influenced by the internal volume, residence time, cooling ability, and stirring ability of an extruder to be employed. When a commercially availabe extruder model TEX38FSS-20AW-V (mfd. by NIHON SEIKOSHO K. K.) is used, the aqueous solution of maltitol preferably supplied at a rate of 10–30 kg/hour for the reasons that sufficient cooling and kneading are achieved and the maltitol magma discharged has a sufficient hardness, and so on.

After the aqueous solution of maltitol is introduced to the extruder, it is cooled and kneaded in the first zone at a temperature preferably in the range of 50°–90° C. and is then conveyed to the second zone.

The temperature of the aqueous solution of maltitol below 50° C. or exceeding 90° C. is not preferable as a maltitol magma cannot be expected to be formed.

Next, a seed crystal is added in the second zone of the extruder, in which the seed crystal is not necessarily a crystalline mixture solid containing maltitol and a maltitol crystal obtained by the fractionation can also be used.

The quality of maltitol as a seed crystal is preferably but not necessarily the equivalent level of quality to the aqueous solution of maltitol supplied for the reason that the quality control of the product is made easier.

The seed crystal is preferably added and kneaded at the time when the temperature of the aqueous solution of maltitol supplied to the extruder reaches a temperature in the range of 50°–80° C. When the seed crystal is added at a temperature of less than 50° C., the aqueous solution of maltitol is not preferred because of the disadvantages that it has a high viscosity and requires a time for the kneading with the seed crystal, that the speed of crystallization is slow after the formation of maltitol magma, and that a maltitol magma formed has a high ratio of a glassy solid content and affects the shelf stability of a product.

The addition of the seed crystal at a temperature exceeding 80° C. is not preferred for the reasons such as the possibility of dissolution of the seed crystal.

Further, the seed crystal is added at various rates depending on the concentration, introducing rate, quality or addition temperature of the aqueous solution of maltitol. The seed crystal is preferably added at a rate to ensure that the amount to be added is in the range of about 3–80% to the weight (extruded amount) of the maltitol magma extruded in a unit time, since the addition at the rate services the formation of a maltitol magma having an appropriate hardness. When the maltitol magma is typically extruded in an amount of 30 kg/hour, the crystal seed is added at a rate of 0.9–24 kg/hour.

Furthermore, the seed crystal may be added continuously or intermittently.

However, the seed crystal is preferably added continuously for the reason that the homogeneous dispersion of the seed crystal in the aqueous solution of maltitol is advantageous for the formation of the maltitol magma in a short time.

The aqueous solution of maltitol and the seed crystal supplied as described above are subsequently cooled and kneaded in the third and succeeding zone(s) in the extruder. The third and succeeding zone(s) is not necessarily a single zone but may be comprised of a plurality of zones.

When the third and succeeding zone(s) is a single zone, the third zone is a final zone. If the third and succeeding zone(s) is composed of two zones, the fourth zone is a final zone; if the third and succeeding zone(s) is composed of three zones, the fifth zone is a final zone.

The cooling and the kneading are carried out in the above described extruder under such a condition that the final cooling and kneading zone is kept at a temperature in the range of 25°–60° C., a screw is rotated at a speed of about 60 rpm to stay the aqueous solution of maltitol and the seed crystal for about 1–2 minutes within the zone for obtaining a maltitol magma having an appropriate hardness.

Moreover, when the crystalline mixture solid containing maltitol in the form of magma having improved physical properties is discharged from the extruder, any one of the forms such as line, rod, plate or the like can be freely selected. For example, if the crystalline mixture solid containing maltitol is formed in a thin rod, it is preferably discharged at a diameter in the range of 2–6 mm because the following processes, if necessary, such as maturing, rough grinding and drying can be conducted easily.

The crystalline mixture solid containing maltitol having improved physical properties thus obtained has an extensively improved hygroscopicity as compared to crystalline mixture solids containing maltitol prepared by the spray-drying method or the fluidized drying method and also has a uniform growth direction of the maltitol crystal as compared to a crystalline mixture solid containing maltitol prepared by the block grinding method, so that it is excellent in compression properties and a tablet having a high hardness can be obtained even in the case of its direct punching operation.

Moreover, since the powder of the crystalline mixture solid containing maltitol has a large apparent specific gravity, it has excellent properties such that the fine powder is scattered little, only a small container or conveying device is needed for the storage or the conveyance of the powder and a container used for the other sugar alcohols may also be used.

While the crystalline mixture solid containing maltitol having improved physical properties discharged in the form of magma can be made as a product as such, it can be treated by way of for example maturing, rough grinding, drying, pulverization, classification or the like, if necessary, because of the properties of the product on the storage of it or the easiness of handling it.

The crystalline mixture solid containing maltitol in the form of magma having improved physical properties is matured preferably under a condition at 15°–80° C. for about 5–120 minutes, more preferably under a condition at 55°–70° C. for 15–30 minutes for the reasons of the prevention of the combination of a powder product obtained subsequently or the like.

The methods for carrying out maturing are not particularly restricted, and some methods such as blowing hot air along with moving the crystalline mixture solid containing maltitol on a belt of a metal net or maturing in an incubator can be used.

The method and the condition of the rough grinding are not particularly restricted. When the crystalline mixture solid containing maltitol in the form of magma having improved physical properties is discharged in the form of an elongated rod, it is sufficient only to cut the rod into a length of about 5–15 mm.

When rough grinding is carried out, a commercially available grinder such as FEATHER MILL MODEL FM-I (mfd. by HOSOKAWA MICRON K. K.) can be advantageously employed.

Also, drying of the crystalline mixture solid containing maltitol having improved physical properties obtained by the present invention can be carried out with no particular limitaion. When it is intended to control the water content in the product to the range of 1% or less, it is possible to achieve the object in a relatively short time by drying the product at a temperature of about 80° C.–115° C.

It is also possible to conduct drying in two or more operations under various conditions, and it is also possible to apply a pressure in the range from ordinary pressure to reduced pressure.

As the method which can be advantageously employed in the case of carrying out drying, there are mentioned drying methods such as those of a vibrating conveyer type, a disc type, a hopper-dryer type, a drum type and the like.

BRIEF DESCRIPTION OF THE DRAWINGS

FIG. 1 is a scanning electron micrograph of a crystalline mixture solid containing maltitol of the present invention in which (a) is a micrograph magnified to ×200 and (b) is a micrograph magnified to ×1,000.

BEST MODE FOR CARRYING OUT THE INVENTION

Figure 2A:
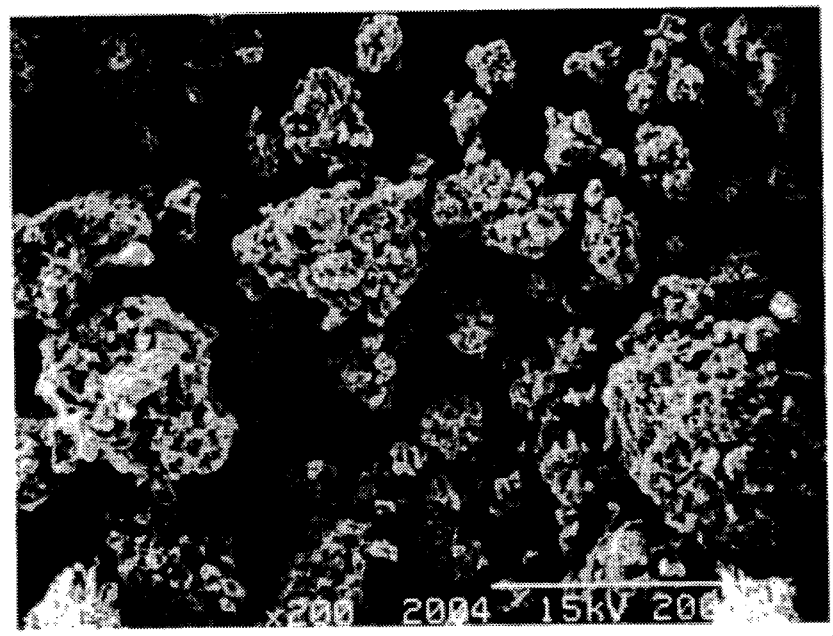
FIG. 2 is a scanning electron micrograph of a conventional crystalline mixture solid containing maltitol in which (a) is a micrograph magnified to ×200 and (b) is a micrograph magnified to ×1,000.

The present invention is described more specifically with reference to the following examples and a comparative example without limit thereto. In the following examples, % means % by weight unless otherwise specified.

EXAMPLE 1

(1) An aqueous solution of maltitol was adjusted to a concentration of 93.5% and was supplied to the first zone of a twin-screw extruder for foods (mfd. by NIHON SEIKO-SHO K. K., TEX-38FSS-20AW-V) at a rate of 22 kg/hour, kneaded at a speed of 60 rpm and conveyed.

The aqueous solution of maltitol having a sugar composition of 1.2% of sorbitol, 94.0% of maltitol and 4.8% of a sugar alcohol having a DP$\geq$3 was used. The aqueous solution of maltitol prior to supply was set at a temperature of 98° C., and the aqueous solution of maltitol in the first zone was adjusted to a temperature of 80° C.

(2) The aqueous solution of maltitol in the second zone of the extruder was adjusted to a temperature of 60° C., and a crystalline mixture solid containing maltitol having the same composition (water content, 0.3%) as that of the aqueous solution of maltitol was supplied at a rate of 8 kg/hour (about 26.7% based on the extruded amount) to form a maltitol magma.

(3) When cooling was conducted so that the temperature of the maltitol magma in the third zone in the extruder was lowered to a temperature of 40° C. and the maltitol magma was extruded at a rate of about 30 kg/hour from a nozzle on which 12 extruding pores having a diameter of 4 mm were open, the maltitol magma extruded had a temperature of 69° C. and a water content of 3.9%.

The maltitol magma obtained had no stickiness in its surface and had so little plasticity that it could be easily broken by bending it by hand.

The average residence time of the content from the first zone to the final zone was for about 1.5 minutes.

(4) The maltitol magma extruded was taken into a stainless tray and matured in a circulating hot air oven (mfd. by TRIO SCIENCE, TR-ED MODEL) at 60° C. for 20 minutes.

(5) The maltitol magma matured was next removed from the oven, cooled to room temperature and ground roughly in a grinder (mfd. by HOSOKAWA MICRON, FEATHER MILL MODEL FM-1).

(6) The product after rough grinding was dried with circulating air for 130 minutes to give a crystalline mixture solid containing maltitol having 0.5% of a water content and improved physical properties.

The time required up to this step was for about 2 hours and 40 minutes, and a crystalline mixture solid containing maltitol was successfully produced in a remarkably short time as compared with that for about 55 hours required for producing a product having the similar quality by the block grinding method.

Moreover, when the crystalline mixture solid containing maltitol was ground, classified and stored in a kraft bag for 1 month, it kept a good powderous state without any caking of powder.

EXAMPLE 2

(1) Similar operations were repeated as in Example 1- (1) except that an aqueous solution of maltitol was adjusted to a concentration of 92.5% and was supplied at a rate of 16 kg/hour, the sugar composition of the aqueous solution of maltitol was adjusted to 1.0% of sorbitol, 90.3% of maltitol and 8.7% of a sugar alcohol having DP$\geq$3, the temperature of the aqueous solution of maltitol prior to supply was set at a temperature of 95° C., and the aqueous solution of maltitol in the first zone was adjusted to a temperature of 65° C.

(2) Similar operations were repeated as in Example 1-(2) except that the aqueous solution of maltitol in the second zone of the extruder was adjusted to a temperature of 55° C., and a crystalline mixture solid containing maltitol (water content, 0.2%) was supplied at a rate of 12 kg/hour (about 42.9% based on the extruded amount) to form a maltitol magma.

(3) When cooling was conducted so that the temperatures of the maltitol magma in the third and fourth zones in the extruder were lowered to the temperature of 45° C. and 38° C., respectively, and the maltitol magma was extruded in the same manner as in Example 1-(3) at a rate of about 28 kg/hour from a nozzle on which 18 extruding pores having a diameter of 3 mm were open, the maltitol magma extruded had a temperature of 67° C. and a water content of 4.1%.

(4) The maltitol magma obtained was matured in the same manner as in Example 1-(4) except that maturing was conducted under a condition at 70° C. for 15 minutes.

(5) The maltitol magma matured was next roughly ground in the same manner as in Example 1.

(6) The product after rough grinding was dried in the same manner as in Example 1-(6) with circulating air under the condition at 90° C. for 180 minutes to give a crystalline mixture solid containing maltitol having 0.6% of a water content and improved physical properties.

EXAMPLE 3

(1) Similar operations were repeated as in Example 1-(1) except that an aqueous solution of maltitol was adjusted to a concentration of 93.0% and was supplied at a rate of 12 kg/hour, the sugar composition of the aqueous solution of maltitol was adjusted to 4.0% of sorbitol, 87.8% of maltitol and 8.2% of a sugar alcohol having DP$\geq$3, the temperature of the aqueous solution of maltitol prior to supply was set at a temperature of 85° C., and the aqueous solution of maltitol in the first zone was adjusted to a temperature of 60° C.

(2) A maltitol magma was formed by repeating the similar operations as in Example 2-(2) except that the aqueous solution of maltitol in the second zone of the extruder was adjusted to a temperature of 55° C., and a crystalline mixture solid containing maltitol was supplied at a rate of 12 kg/hour (about 50% based on the extruded amount).

(3) When cooling was conducted so that the temperatures of the maltitol magma in the third and fourth zone in the extruder were lowered to the temperature of 38° C. and 35° C., respectively, and the maltitol magma was extruded in the same manner as in Example 1-(3) at a rate of about 24 kg/hour from a nozzle on which 18 extruding pores having a diameter of 3 mm were open, the maltitol magma extruded had a temperature of 62° C. and a water content of 4.9%.

The maltitol magma thus obtained was sticky on its surface and also had plasticity, but after several minutes from the extrusion it could be handled so easily as to be broken by bending it by hand.

(4) The maltitol magma obtained was matured in the same manner as in Example 1-(4) except that maturing was conducted under a condition at 60° C. for 30 minutes.

(5) The maltitol magma matured was next roughly ground in the same manner as in Example 1-(5).

(6) The product after rough grinding was dried in the same manner as in Example 1-(6) with circulating air under the conditions of first at 85° C. for 200 minutes and then at 105° C. for 100 minutes to give a crystalline mixture solid containing maltitol having 0.6% of a water content and improved physical properties.

EXAMPLE 4

(1) Similar operations were repeated as in Example 1-(1) except that an aqueous solution of maltitol was adjusted to a concentration of 89.0% and was supplied at a rate of 11.4 kg/hour, the sugar composition of the aqueous solution of maltitol was adjusted to 1.0% of sorbitol, 95.2% of maltitol and 3.8% of a sugar alcohol having DP$\geq$3.

(2) A maltitol magma was formed by repeating the similar operations as in Example 1-(2) except that a crystalline mixture solid containing maltitol (water content, 0.5%) was supplied at a rate of 13.7 kg/hour (about 54.6% based on the extruded amount).

(3) After the same operations as in Example 1-(3) was repeated, a maltitol magma having a temperature upon extrusion at 65° C. and a water content of 3.1% was obtained.

(4) The maltitol magma thus obtained was matured under the same conditions as in Example 1-(4).

(5) The maltitol magma matured was next roughly ground in the same manner as in Example 1.

(8) The product after rough grinding was dried in the same manner as in Example 1-(6) to give a crystalline mixture solid containing maltitol having 0.5% of a water content and improved physical properties.

COMPARATIVE EXAMPLE

The crystalline mixture solid containing maltitol having improved physical properties obtained in Example 1 and maltitol obtained thereby were set as the products of the present invention, and a crystalline mixture solid containing maltitol as a control product was prepared by the conventional method as described below in order to compare it with the product of the present invention.

The aqueous solution of maltitol having the same sugar composition as that in Example 1 was adjusted to a concentration of 88%, and the concentrate was transferred into a crystallizer, adjusted to a temperature of 50° C., added with anhydrous crystals of maltitol as seed crystals in an amount of 2% by weight, and kept for 2 hours under gentle stirring conditions. The content was then placed in a tray where it was allowed to stand for 4 days to effect deposition and solidification. The deposited solid was then removed from the tray and pulverized by a crusher equipped with a scrapper. The resultant powder was dried to give 20 kg of a crystalline mixture solid containing maltitol which contained anhydrous crystals of maltitol (control product).

The product of the present invention and the control product were photographed at 200 magnifications and at 1,000 magnifications with a typical scanning electron microscope.

Figure 2B:

FIG. 1 is a scanning electron micrograph of the product of the present invention in which (a) is a micrograph magnified to ×200 and (b) is a micrograph magnified to ×1,000; and FIG. 2 is a scanning electron micrograph of a conventional crystalline mixture solid containing maltitol in which (a) is a micrograph magnified to ×200 and (b) is a micrograph magnified to ×1,000.

When FIGS. 1 and 2 are compared, it can be confirmed that the product of the present invention has a crystal structure relatively tight as compared with that of the conventional product.

Samples having a particle diameter in the range of 50 mesh–20 mesh were prepared for the product of the present invention and the control product, respectively, and apparent specific gravity and oil absorptivity were measured for these samples.

In this connection, the oil absorptivity was measured by the following procedures.

Castor oil was added to 15 g of a powder sample, and after 5 minutes the mixture was placed in a centrifugal tube (provided with pores on the bottom) in which a filter cloth was spread and centrifuged at 1,300 G for 10 minutes. The weight of cakes remained on the filter cloth was measured, and the oil absorptivity was calculated from the following equation:

Oil absorptivity (%)={[(weight of cakes)−15]/15}×100

The results of the measurements are shown in Tabel 1.

TABLE 1

|  | Product of the invention | | Control product | |
| --- | --- | --- | --- | --- |
|  | ca. 20 mesh | ca. 50 mesh | ca. 20 mesh | ca. 50 mesh |
| Apparent specific gravity | 0.72 | 0.61 | 0.49 | 0.45 |
| Oil absorptivity | 7.5% | 16.5% | 20.8% | 22.0% |

It can be confirmed from Table 1 that the product of the present invention has an apparent specific gravity heavier than that of the control product and an oil absorptivity lower than that of the control product.

As desribed above, the crystalline mixture solid containing maltitol according to the present invention which has improved physical properties has a crushed and comparatively tight crystal structure which can be observed by 1,000 magnifications as compared with the crystalline mixture solid containing maltitol obtained by the conventional method. The crystalline mixture solid containing maltitol according to the present invention has a high apparent specific gravity in the same level as that of sorbitol as one of the other sugar alcohols and also a low oil absorptivity.

Thus, (a) the crystalline mixture solid containing maltitol of the present invention is not bulky in volume and requires no packaging material or packaging container for its exclusive use, so that packaging materials or packaging containers for the other sugar alcohols can be used and a large space or conveying apparatus is not required for the storage or conveyance of it;

(b) the powder of it is heavy in weight and thus the fine powder is hardly scattered, so that it can be used for a variety of applications; and (c) it has a tight crystal structure, so that a tablet prepared by the direct punching of it is excellent in hardness.

Also, according to the process for preparing the crystalline mixture solid containing maltitol of the present invention, a crystalline mixture solid containing maltitol having improved physical properties can be prepared in a very short time by simple processes without complicated operations and thus places and containers for the storage of intermediates in the middle of the crystallization can be drastically reduced, so that the automating of the process can be conducted easily.

What is claimed is:

1. A crystalline mixture solid containing maltitol, comprising
   a) having a crushed and relatively tight crystal structure which can be observed by a scanning electron microscope with magnifying power of ×1000,
   b) having an apparent specific gravity of said crystalline mixture solid containing maltitol having a particle size from 50 mesh to 20 mesh in the range of 0.650–0.750,
   c) having an oil absorptivity of said crystalline mixture solid containing maltitol having a particle size from 50 mesh to 20 mesh in the range of 7.0%–17%, and
   d) having a melting point of said crystalline mixture solid containing maltitol in the range of 134°–145° C.

2. A crystalline mixture solid containing maltitol according to claim 1, wherein the solid component comprises maltitol in the range of 80–98% by weight, sorbitol in the range of 0.5–15% by weight, and maltotriitol and sugar alcohols, having a degree of polymerization of DP≧3, in the range of 1.5–10% by weight.

3. A crystalline mixture solid containing maltitol having a melting point in range of 134°–145° C. which is prepared by supplying an aqueous solution of maltitol to an extruder provided with elongated cooling and kneading zones, cooling and kneading the aqueous solution of maltitol in the presence of seed crystals to form a maltitol magma, and extruding continuously said magma from a nozzle.

4. A crystalline mixture solid containing maltitol having a melting point in the range of 134°–145° C. which is prepared by continuously supplying an aqueous solution of maltitol having a concentration in the range of 80–98% by weight and a maltitol content in the solid component in the range of 80–99% by weight to the first zone of an extruder provided with elongated cooling and kneading zones, cooling and kneading the aqueous solution of maltitol to 50°–90° C., continuously or intermittently conducting the addition and kneading of seed crystals in an amount of 3–80% by weight based on the extruded amount to the second zone in which said aqueous solution of maltitol has been cooled to a temperature of 50°–80° C., further continuing cooling and kneading in the continuous third zone, cooling and kneading to a temperature of 25°–60° C. in the final zone, and continuously extruding a maltitol magma thus formed from the extrusion nozzle.

5. A crystalline mixture solid containing maltitol having a melting point in the range of 134°–145° C. which is prepared by sequentially passing through the following steps of a) the first step in which an aqueous solution of maltitol having a concentration of 80–98% by weight and a solid composition comprising 0.5–15% by weight of sorbitol, 80–98% by weight of maltitol and 1.5–10% by weight of maltotriitol and sugar alcohols having a molecular weight not less than that of maltotriitol (DP≧3) is continuously supplied to the first zone provided with elongated cooling and kneading zone, cooling and kneading to a temperature of 50°–90° C. is conducted, the addition and kneading of seed crystals in an amount of 3–80% by weight based on the extruded amount to the second zone in which temperature reached 50°–80° C. are continuously or intermittently conducted, cooling and kneading are further continued in the continuous third zone, the mixture is cooled and kneaded to a temperature of 25°–60° C. in the final zone, and a maltitol magma formed is extruded from extrusion nozzle, b) the second step in which said maltitol magma extruded is matured at 15°–80° C. for 5–30 minutes, and c) the third step in which the matured maltitol magma is then roughly ground, dried under the conditions at 80°–115° C. for 60 minutes or more pulverized and classified.

* * * * *